United States Patent
Gerigk

(10) Patent No.: US 9,677,978 B2
(45) Date of Patent: Jun. 13, 2017

(54) FIXATIVE SOLUTION, FOR FIXATION AND PRESERVATION OF BIOLOGICAL SAMPLES

(75) Inventor: Roberto Gerigk, Itú, São Paulo (BR)

(73) Assignee: José Carlos Lapenna, Itú, São Paulo (BR)

(*) Notice: Subject to any disclaimer, the term of this patent is extended or adjusted under 35 U.S.C. 154(b) by 295 days.

(21) Appl. No.: 14/115,141

(22) PCT Filed: May 2, 2011

(86) PCT No.: PCT/IB2011/051937
§ 371 (c)(1),
(2), (4) Date: Jan. 15, 2014

(87) PCT Pub. No.: WO2012/150479
PCT Pub. Date: Nov. 8, 2012

(65) Prior Publication Data
US 2014/0162246 A1    Jun. 12, 2014

(51) Int. Cl.
  A01N 1/00    (2006.01)
  G01N 1/30    (2006.01)
(52) U.S. Cl.
  CPC ..................... G01N 1/30 (2013.01)
(58) Field of Classification Search
  CPC ....................................... A01N 1/00
  See application file for complete search history.

(56) References Cited

U.S. PATENT DOCUMENTS

| | | | |
|---|---|---|---|
| 3,689,660 A * | 9/1972 | Burk | A01N 37/34 514/527 |
| 4,100,158 A | 7/1978 | Hydes et al. | |
| 4,163,797 A * | 8/1979 | Burk | A01N 37/34 514/210.17 |
| 4,241,080 A | 12/1980 | Burk | |
| 5,422,277 A | 6/1995 | Connelly et al. | |
| 5,912,389 A | 6/1999 | Matsumoto | |
| 6,531,317 B2 | 3/2003 | Guirguis et al. | |
| 2005/0084924 A1 | 4/2005 | Shults et al. | |
| 2008/0102094 A1 * | 5/2008 | Bryant | A01N 47/40 424/409 |

FOREIGN PATENT DOCUMENTS

| | | |
|---|---|---|
| DE | 26 30 823 A1 | 1/1977 |
| DE | 38 22 183 A1 | 2/1990 |
| DE | 38 24 936 A1 | 3/1990 |
| DE | 44 04 544 A1 | 8/1995 |
| DE | 699 17 779 T2 | 6/2005 |
| EP | 0 953 284 A1 | 11/1999 |
| EP | 1 455 174 B1 | 12/2004 |
| WO | WO 03/029783 A1 | 4/2003 |
| WO | WO 2012/150479 A1 | 11/2012 |

OTHER PUBLICATIONS

International Search Report of PCT/IB2011/051937, Feb. 13, 2012.

* cited by examiner

*Primary Examiner* — Ruth Davis
(74) *Attorney, Agent, or Firm* — D'Ambrosio & Menon, PLLC; Usha Menon

(57) ABSTRACT

A fixative solution, suitable for fixation of biological materials such as human or veterinary biological tissues, cells, organs and secretions as well as bacteria, viruses, yeasts, parasites and biotech products such as embalming articles. The fixative solution is not a dangerous product according to European standards, and it contains low concentration of aldehydes or heavy metals, rendering a product that cannot be considered dangerous. Even so, biological samples can be optimally preserved and fixed with this solution.

12 Claims, No Drawings

FIXATIVE SOLUTION, FOR FIXATION AND PRESERVATION OF BIOLOGICAL SAMPLES

CROSS REFERENCE TO RELATED APPLICATIONS

This application is the National Stage of PCT/IB2011/051937 filed on May 2, 2011, the disclosure of which is incorporated by reference. The international application under PCT article 21(2) was published in English.

The invention refers to a fixative solution, suitable for fixation of biological materials such as human or veterinary biological tissues, cells, organs and secretions as well as bacteria, viruses, yeasts, parasites and biotech products such as embalming articles. New in this invention is the property of this fixative solution not to be a dangerous product towards European standards. It contains low concentration of aldehydes or heavy metals, rendering a product that cannot be considered dangerous. Even so, biological samples can be optimally preserved and fixed with this solution.

Another advantage of this solution lies in the fact that there is not such a strong reaction between the sample and the new fixing solution. With this, the sample is set intact and fixed until further processing, and proteins and other components from the sample are not strongly altered by the solution, enabling the detection of biochemical factors that would be destroyed in a conventional fixative solution.

Typical for formaldehyde, chromic acid, osmic acid and other components attachable, is the irreversible denaturation of proteins, which has a decisive influence on the proteins composition of the sample.

In the biochemical determination of enzymes, proteins and immunological and other protein-specific examinations, these conventional fixative substances cannot be used.

Until the present day, formaldehyde (formalin) is the most used fixative substance, which has excellent fixative properties even for longer periods of time.

Aldehydes, especially formaldehyde, are considered highly toxic.

It was classified as a justified potential carcinogen chemical and it can cause allergies and dermal, respiratory and eye irritations. In case of exposure to high doses, it can even result in death risk. It also has a characteristic pungent and unpleasant odor.

For reasons of environmental protection and work safety, the use of formalin is legally restricted.

PRIOR ART

Fixative solutions without formaldehyde are known front patents EP 1 455 174 B1, U.S. Pat. No. 6,531,317B2, WO 03/029 783 A1, DE 699 17 779 T2, U.S. Pat. No. 5,422,277A, US 2005/0084924 A1e DE 26 30 823 A1.

There are several ideas to create a festive solution without formaldehyde, such as described in DE 38 22 183 A1, where Tannic Acid is suggested as the main component of the solution. To obtain a quick fixation the patent DE 38 24 936 A1 suggests the utilization of hot water action, with the aid of Tannic Add and a Bi-alcohol in the water. The patent DE 44 04 544 A1 rejects entirely chemical means of fixation, such as formalin, suggesting a denaturation of proteins from the sample by the action of heat through hot water baths. This procedure has the disadvantage, however, that the structures of the material that is being fixed may undergo morphological changes. Proteins, for example, can clot. For this reason, this procedure is not suitable for all types of materials.

Other fixative solutions are known in the literature. Almost all of them, with few exceptions, contain very dangerous substances and are a great potential hazard to living beings and the environment.

Among the best known we can include:

Schaudinn's Fixative (it contains mercury salts), SAF (it contains formaldehyde), MIF (it contains formaldehyde and mercury salts), osmic acid (it is carcinogenic, toxic, caustic), chromic acid, (carcinogenic, toxic, caustic), FA (formaldehyde and alcohol) and others which are mentioned in the literature.

In general, a fixative solution must maintain biological materials such as biological tissues, cells, clustering of cells, viruses, bacteria, parasites, yeasts, feces and other in a stable state for a relatively long period of time after taking the sample. The original state of the sample immediately after collection should be fixed for a further examination in the laboratory (e.g., a microscopic, examination) so morphological state present at the collection of the sample can be found. Importantly, the morphological structure of the sample must be preserved. There shall be no chemical, physical or microbiological processes or proliferation of bacteria, yeast or fermentation or decomposition processes or other degradation processes, which may adversely affect the sample.

In short, the fixative solution should keep any type of biological material in a stable state suitable for preparation or analytical purposes.

The ideas previously described which are in the current-state of the art, are oriented to avoid completely the use of formalin, replacing it by nontoxic substance or less hazardous ones, although they show as much as possible the same characteristics that formalin fixation does.

The fixation is based on different chemical mechanisms, some of which are not yet fully elucidated. One major mechanism is the so-celled "Crossing Over". In this process, there is a chemical bond of the molecule in the fixative which can be covalent type, Van-der-Waals interaction or even ionic to a corresponding position in a protein molecule in a sample. It is possible that there are different types of bonding at the same time. With the raise of chemical bondings in biological material there is an increase in the mechanical stability of biological structures and at the same time microorganisms in the sample are destroyed.

Until now, fixative solutions were designed to maximize these processes. With this, there is always an excess of fixative substance in the solution, which is not always necessary or even convenient. (If there is excess of toxic substances in the workplace, there will be excessive reaction with the sample.)

OBJECTIVE OF THE INVENTION

The task of the present invention is to create a fixative solution which is not dangerous, and has the qualities of formalin in milder form. A composition with other fixative substances should be possible to an adjustment of the ideal fixation process.

This task is solved through the features of Patent Claim listed under Item 1. Other developments or advantageous presentations may be removed from the sub-Claim submitted.

DETAILED DESCRIPTION OF THE INVENTION

The invention consists of providing a fixative solution that:
  Is in accordance with valid rules (in this case rules of the European community) the solution is not dangerous or just little dangerous to the user and the environment. (In any case less dangerous than the traditional fixation solutions).
  Does not present other forms of danger (flammable, explosive, corrosive, accumulating in the environment or highly volatile).
  Reacts in a mild way with the sample and the sample proteins, causing no strain on the morphological structure of the sample ("shrinkage") and keeps intact more biological and biochemical parameters than traditional solutions.
  Does not significantly disturb the processes in which the sample has to undergo after fixation (such as unwanted reactions, preventing staining and others).

Two basic substances were chosen to produce the desired effect:
  Halogen cyano-acetamides
  2,2-dibromo-2-cyano Acetamide or 2,2-Dibromo-3-nitrilopropionamide or for short DBNPA
  In order to simplify, we will call the mentioned substance as DBNPA.

These substances were chosen because of the following:
Halogen cyano-acetamides and DBNPA have strong biocidal properties and completely interrupt the biological and microbiological activities in the sample.

Because the molecular structure of these substances, the effect of crossing over can occur because these halogen atoms produce molecular polarization needed to the occurrence of interactions van-der-Waals between the molecule of fixative and protein molecules of the sample, thereby ensuring stabilization of the structure and thus fixation. Due to high biocidal properties of the substance, minimum concentration may be applied, avoiding unnecessary excesses. The biological activity of the sample ceases quickly, avoiding the microbiological degeneration of the sample.

The optimal action of the solution occurs at acid pH or around the neutral point, but depending on other components of the solution and the desired results, it can be required adjusting the pH to a range from 3-9.

The fixative solution which is dealt by the present invention can be prepared in liquid form ready. However, it is also possible to present it in a concentrated form which provides a turnkey solution, after addition of an appropriate solvent, which in the simplest case is water. This (concentrate) can be a concentrated solution, a powder mixture, a soluble gel, a tablet, a soluble capsule, a soluble varnish covering the container with the solution or another similar form.

With this transportation, storage and packaging costs can be reduced, besides other advantages of economic order and logistics as the solvent, water in most cases, can be added to the final destination by the user.

A concrete example is a solution using 2% by weight DBNPA, and other substances as an additional acid to adjust pH to slightly acidic. Organic or inorganic acids can be utilized such as citric acid. Following a moisturizer can be added, such as Ethylene Glycol, Glycerin, Propylene Glycol, Sorbitol, Erythriol or similar, which also serve as mediators to the lipid phase of the sample, facilitating its spread. Another component to be added would be an ionic or anionic surfactant, or a mixture of both, in order to lower the surface tension of the solution, improving the dispersive features. From these substances we can list ethoxylated polyethylene glycol, ethoxylated sorbates (commercially TWEEN), sodium dodecyl sulfate, sodium benzene sulphonate and other Alkyl sulfates and sulphonates, as well as commercial products in the series TRITON, ETHOMEEN and other similar ones. Fatty alcohols (N>8) such as mono or polyalcohols, linear or branched, can be applied as process aids and mediators of the surfactants used.

For improvement of the solution for marketing purposes, flavorings and colorings that do not conflict with other components will be added.

For isotonic adjustment purposes salts of alkali metals or alkaline earth such as chlorides, sulfates, nitrates, citrates, acetates of lithium, sodium, potassium, magnesium, calcium, strontium, or others.

For pH adjustment purposes in certain applications, it may be necessary the utilization of buffer solutions such as citrate buffer, acetate or others known in literature.

Solution Stabilization Additives:

It is known from literature that halogeno cyano acetamides, especially DBPNA undergo alkaline hydrolysis when in solution. For the solution to guarantee a longer period operation, small amounts of specific antioxidants should be added to the solution to avoid an early deterioration. The solution thus treated, maintains its activity for a period of about two years. The degradability of the solution when disposed is not affected, maintaining its ecological feature.

As we can see in the diagram below, the final decomposition products of DBPNA are not accumulative in the environment:

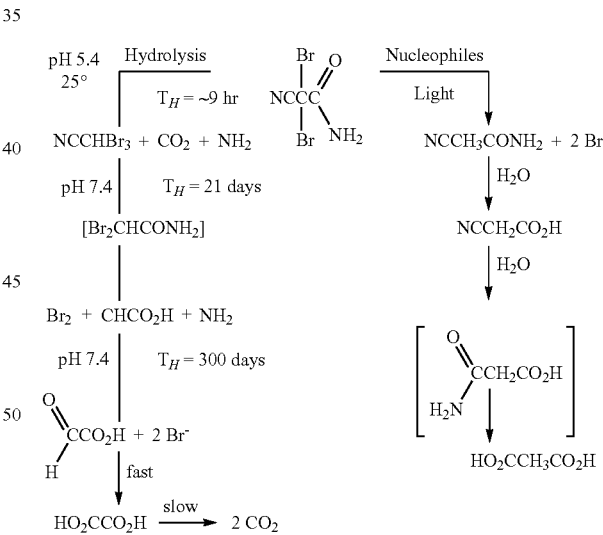

Photodecomposition is delayed with the use of a dye-ink in the solution, and the recommendations of storage in dark and fresh place.

The hydrolysis is greatly reduced with the use of commercial antioxidants such as 4,4-bis (2,6-di-tert-butylphenol) or 2,6-di-tert-butyl-p-cresol or similar ones, which is practiced commercially.

It is important to highlight that formaldehyde is one of the decomposition products from DBPNA, is inhibited, due to stabilization by antioxidants. For the users, who need their biological sample to be fixed for a processing that by rule it takes only a few weeks the solution does not present levels of formaldehyde that may affect the mild fixation.

Commercial biocides solutions of DBPNA used in the paper and textile industry thus stabilized show a degradation of DBPNA fewer than 10% in 20 months, ensuring an optimal action of the component.

Simple Formulation Example:

| | |
|---|---|
| DBPNA | 2% |
| Propylene Glycol | 5% |
| TWEEN 80 | 1% |
| Food coloring | 0.01% |
| Mixture of fragrances | 0.01% |
| Antioxidant | 0.05% |

Water to make 100%

This solution was tested and evaluated with samples of human and animal feces from the parasitological point of view; eggs of parasites were mainly detected. Histological samples from bovine muscle were also fixed, showing excellent quality of fixation and preservation. During the 30 days observation period, no changes were observed in any of the analyzed samples. In a subsequent evaluation, human feces samples were found contaminated with protozoa. The report for this Evaluation is attached to this document. Protozoa in feces are extremely susceptible to degradation and can degenerate in a few hours. In the tests a preservation and fixation was demonstrated for a period exceeding seven days. Compared to a standard solution of formaldehyde, the quality of preservation was equal if not better.

Example of Soluble Tablet Simple Formulation:

| | |
|---|---|
| DBPNA | 100 g |
| Sorbitol powder | 41 g |
| TWEEN 80 | 2.5 g |
| Citric Acid | 2.0 g |
| Food coloring | 1.0 g |
| Mixture of fragrances | 1.0 g |
| Antioxidant | 2.5 g |
| Gum arabic | 50 g |
| Total Mass | 200 g |

One 40 g-tablet of this mass contains 20 g of DBPNA used to produce 1 liter of 2% solution ready-to-use At 2% concentration of DBPNA in the solution should bring only the risk phrase 43, indicating the risk of sensitization through skin contact. At concentrations below 1% solution does not need indication as dangerous product.

It is not flammable, corrosive, does not produce toxic or dangerous emanations, it is not teratogenic or carcinogenic, is not offensive to the environment and it requires no special precautions for work safety, bringing about an extraordinary improvement in job security for the user as well as a remarkable simplification in the processes of environmental management in the laboratory in which it is being utilized.

It should be stated here that, besides water, other solvents may be utilized, depending on the desired application. With advances in diagnostic techniques, alcohol and other solvents such as methyl, ethyl, propyl, butyl, ketones, esters, ethers, glycerin and other organics are being discussed. The fixative described can be obtained with the use of organic solvents and mixtures of organic solvents or mixtures of organic solvents with water.

The invention claimed is:

1. A method comprising: fixing and preserving biological materials by placing said materials in a composition comprising halocyanoacetamide and a pH adjuster selected from the group consisting of acetic acid, phosphoric acid, citric acid, and formic acid.

2. The method according to claim 1, wherein the halocyanoacetamide is 2,2-dibromo-2-cyanoacetamide.

3. The method according to claim 1, wherein the composition additionally comprises a solvent selected from water, organic solvents or mixtures thereof.

4. The method according to claim 1, wherein the composition has a pH adjusted to a range between pH 3.0 and pH 6.0.

5. The method according to claim 1, wherein the composition additionally comprises:
a humectant;
a surfactant;
a salt of alkali metals or alkaline earth metals;
an antioxidant;
and
dyes.

6. The method according to claim 5, wherein the humectant is selected from the group consisting of
ethylene glycol,
propylene glycol,
glycerine,
erithriol,
sorbitol,
and mixtures thereof.

7. The method according to claim 5, wherein the surfactant is selected from the group consisting of
non-ionic surfactants,
sodium dodecyl sulphate and mixtures thereof.

8. The method according to claim 5, wherein the alkali metals and alkaline earth metal salts are selected from the group consisting of citrates, acetates, phosphates, chlorides, sulphates, formates, and nitrates of lithium, sodium, potassium, caesium, magnesium, calcium, strontium and barium, and mixtures thereof.

9. The method according to claim 5, wherein the antioxidant is selected from the group consisting of 4,4-bis(2,6-di-tert-butylphenol) 4,4-bis(2,6-di-tert-buthyl-p-cresol) and mixtures thereof.

10. The method according to claim 5, wherein the composition comprises:
0.05%-5% 2,2-dibromo-2-cyano acetamide, citric acid, 1%-30% propylene glycol, 0.01%-5% non-ionic surfactants, 0.001%-01% dye, 0.05%-0.1% antioxidant 4,4-bis (2,6-di-tert-butylphenol), and 0.01-10% sodium chloride.

11. The method according to claim 5, wherein the composition comprises:
1% 2,2-dibromo-2-cyanoacetamide, 0.5% citric acid, 12% propylene glycol, 0.1% non-ionic surfactants, 0.05% aromatic oils, 0.05% antioxidant 4,4-bis(2,6-di-tert-butylphenol) 0.01% dye, and 0.1% sodium chloride.

12. The method according to claim 1, wherein the composition is is a powder, tablet, capsule, gel, or varnish.

* * * * *